US006492147B2

(12) United States Patent
Imamura et al.

(10) Patent No.: US 6,492,147 B2
(45) Date of Patent: Dec. 10, 2002

(54) METHOD FOR PRODUCING MICROBIAL POLYESTER

(75) Inventors: Takeshi Imamura, Chigasaki (JP); Tetsuya Yano, Atsugi (JP); Shin Kobayashi, Kawasaki (JP); Sakae Suda, Ushiku (JP); Tsutomu Honma, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/740,021

(22) Filed: Dec. 20, 2000

(65) Prior Publication Data

US 2001/0031488 A1 Oct. 18, 2001

(30) Foreign Application Priority Data

Dec. 27, 1999 (JP) ............................. 11-371872

(51) Int. Cl.$^7$ ................................. C12P 7/62
(52) U.S. Cl. .................. 435/135; 435/142; 435/146; 435/280; 435/874; 435/875; 435/876; 435/877; 528/354; 528/361
(58) Field of Search ................ 435/135, 142, 435/146, 280, 874–877; 528/354, 361

(56) References Cited

U.S. PATENT DOCUMENTS 5,290,910 A  3/1994  Shiotani et al. ............. 528/361
5,344,769 A  9/1994  Witholt et al. ............... 435/135

FOREIGN PATENT DOCUMENTS

EP  0247151  7/1988
EP  0526850  2/1993
JP  5-000159  1/1993
JP  5-030980  2/1993

OTHER PUBLICATIONS

Lageveen, et al; "Formation of Polyesters by *Pseudomonas oleovorans*: Effect of Substrates on Formation and Composition of Poly–(R)–3–Hydroxyalkenoates and Poly–(R)–3–Hydroxyalkenoates", Appl. & Environ. Microb., 54, 12 (1988) 2924–2932.

Fritsche et al., "Production of Unsaturated Polyesters by *Pseudomonas Oleovorans*", Int.. Biol. Macromol., 1990, vol. 12, pp. 85–91.

Huijberts, et al., "*Pseudomonas putida* . . . Unsaturaded Monomers", Appl. & Envir. Microbiol., Feb. 1992, vol. 58, No. 2, Feb. pp. 536–544.

G.J. M. de Koning, "A Biodegradable rubber . . . Oleovorans", Polymer vol. 35, No. 10, 1994, pp. 2090–2097.

Ashby et al., "Radiation crosslinking . . . from tallow", Int,. J. Biol. Micromol., vol. 23, (1998) pp. 61–72.

U.S. application No. 09/745,476, Honma filed Dec. 26, 2000, pending.

*Primary Examiner*—Leon B. Lankford, Jr.
*Assistant Examiner*—Kailash C. Srivastava
(74) *Attorney, Agent, or Firm*—Fitzpatrick, Cella, Harper & Scinto

(57) ABSTRACT

A method for producing a microbial polyester by culturing a microorganism being capable of producing a poly hydroxyalkanoate polyester in a culture medium containing 1-hexene as a sole carbon source.

7 Claims, 2 Drawing Sheets

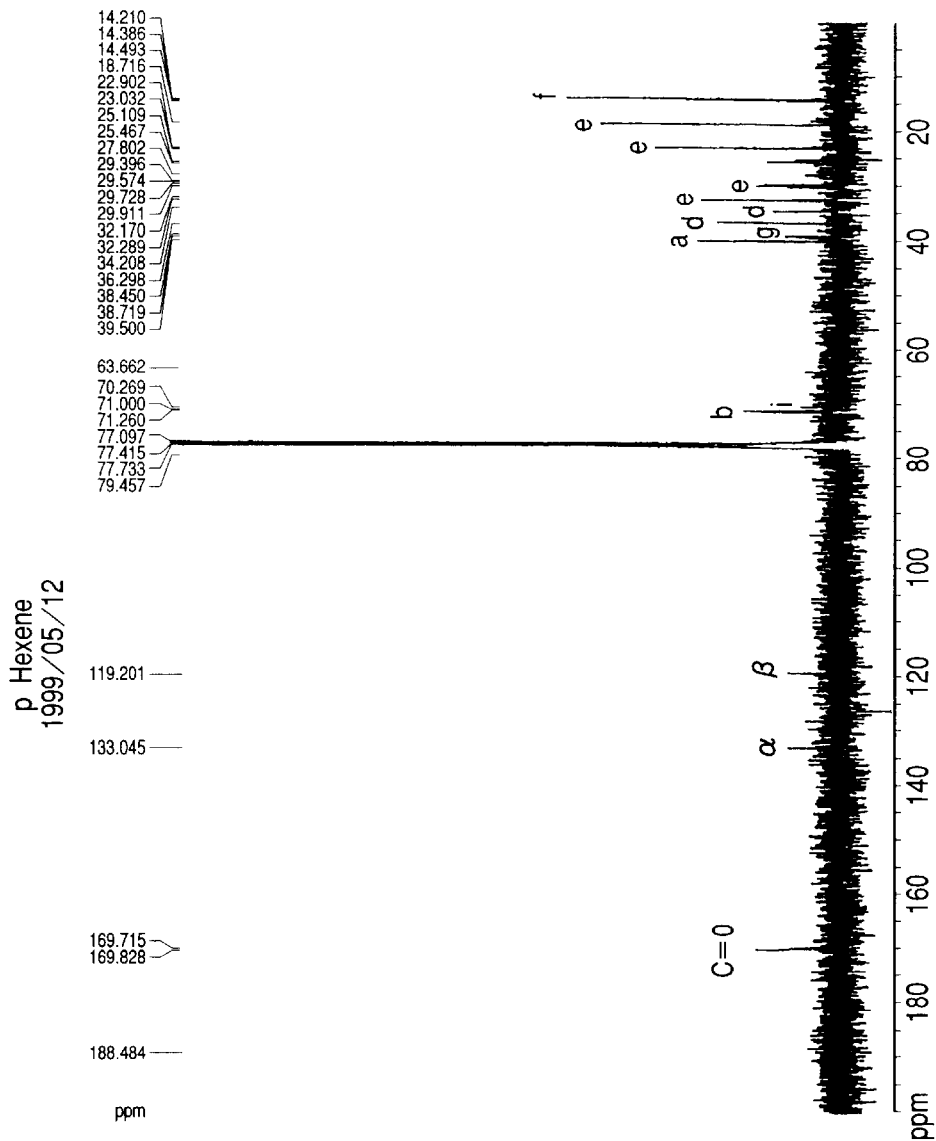

METHOD FOR PRODUCING MICROBIAL POLYESTER

BACKGROUND OF THE INVENTION

1. Field of the Invention

The present invention relates to a production method of a polyester by using a microorganism.

2. Related Background Art

Microbial polyesters represented by poly 3-hydroxybutyrate (PHB) have a remarkable feature that they are biologically degradable, differing from the synthetic polymers made from petroleum.

Synthetic polymers have been used as plastics etc. for a long time. On disposal, however, this feature of hard-to-decompose makes them accumulated in waste-disposal facilities, or when they are burned, harmful substances such as dioxin and endocrine-disruptors are generated to cause environmental pollution.

On the other hand, polyesters produced by microorganisms (hereinafter referred to as "microbial polyesters") can be biologically degraded to be incorporated in a natural recycling system, usable as environment-maintaining plastics. They also have a potential as soft materials for medical use (Japanese Patent Application Laid-Open No. 5-159).

Heretofore, various bacteria have been reported to produce and accumulate PHB or copolymers of other hydroxyalkanoic acids in the cells (Handbook of Biodegradable Plastics, ed. by Biodegradable Plastics Society, published by N.T.S., p. 178–197 (1995)).

Recently, for industrial use of such poly hydroxyalkanoic acids (PHA), various attempts have been done to make the microorganisms produce modified PHA comprised of unusual monomer units for broader physicochemical properties.

One of these attempts, Japanese Patent Application Laid-Open No. 5-30980, discloses that *Pseudomonas fluorescence* FA-031 (FERM P-3433) can produce copolymers of poly hydroxyfatty acid esters made of monomer units of C4 to C16, when the cells are cultured using oleic acid, triolein (olive oil) or triglyceride as a carbon source under nitrogen starvation. The presence of carbon-carbon double bonds were confirmed in C14 and C16 units.

Further, it discloses that when linoleic acid is used as a substrate, the produced polyester is comprised of units of C4 to C16, the presence of double bond was confirmed in units of C10, C12, C14, and C16, and when α-linolenic acid is used as a substrate, the produced polyester is comprised of units of C4 to C16, the presence of double bonds were confirmed in units of C8, C10, C12, C14, and C16.

A method to produce PHA containing units of 3-hydroxyoctenoic acid and 3-hydroxyhexenoic acid is disclosed in Int. J. Biol. Macromol. Vol,12 p. 85–91 (1989), where *Pseudomonas oleovorans* ATCC 29347 is grown using 3-hydroxy-6-octenoic acid or 3-hydroxy-7-octenoic acid as a substrate.

A method to produce PHA containing units of 3-hydroxydecenoic acid and 3-hydroxytetradecenoic acid is disclosed in Appl. Environ. Microbiol. (1992) Vol. 58(2) p. 536–544, where *Pseudomonas putida* KT2442 is grown using glucose, fructose and glycerol as substrates.

A method to produce PHA containing units of 3-hydroxyoctenoic acid and 3-hydroxyhexenoic acid is disclosed in Polymer, Vol 35(10) (1994) p. 2090–2097, where *Pseudomonas oleovorans* ATCC 29347 is grown using n-octane and 1-octene as substrates.

A method to produce PHA containing units of 3-hydroxydecenoic acid and 3-hydroxytetradecenoic acid is disclosed in Int. J. Biol. Macromol. 23 (1994) p. 61–72 where *Pseudomonas resinovorans* NRRL B-2649 is grown using tallow as a substrate.

Although various methods have been studied to produce PHA having carbon-carbon double bonds in their side chains using microorganisms as described above, the inventors have come to think that more variety of the culture conditions and substrates are required for practical use. At present, studies on the use of organic substrate materials derived from relatively inexpensive minerals such as petroleum are not at least sufficient.

SUMMARY OF THE INVENTION

According to one embodiment of the present invention, there is provided a method for producing microbial polyester which comprises a step of growing a microorganism capable of producing a polyester in a medium containing 1-hexene as a sole carbon source.

Preferably, at least one monomer unit constituting the polyester is a hydroxyfatty acid having a carbon double bond, more preferably, at least one of 3-hydroxyhexenoic acid and 3-hydroxyocteinoic acid.

Preferably, the microorganism is a bacterium of genus Pseudomonas, more preferably, *Pseudomonas cichorii* YN2 (FERM BP-7375).

The method of the present invention further comprises a step of recovering the polyester product from the microorganism in the culture medium.

The method of the present invention enables the production of poly hydroxyalkanoate containing 3-hydroxyfatty acid having a double bond in the side chain by using 1-hexene as a sole carbon source.

BRIEF DESCRIPTION OF THE DRAWINGS

FIG. 2 is a $^{13}$C-NMR chart of PHA.

DETAILED DESCRIPTION OF THE PREFERRED EMBODIMENTS

Figure 1:
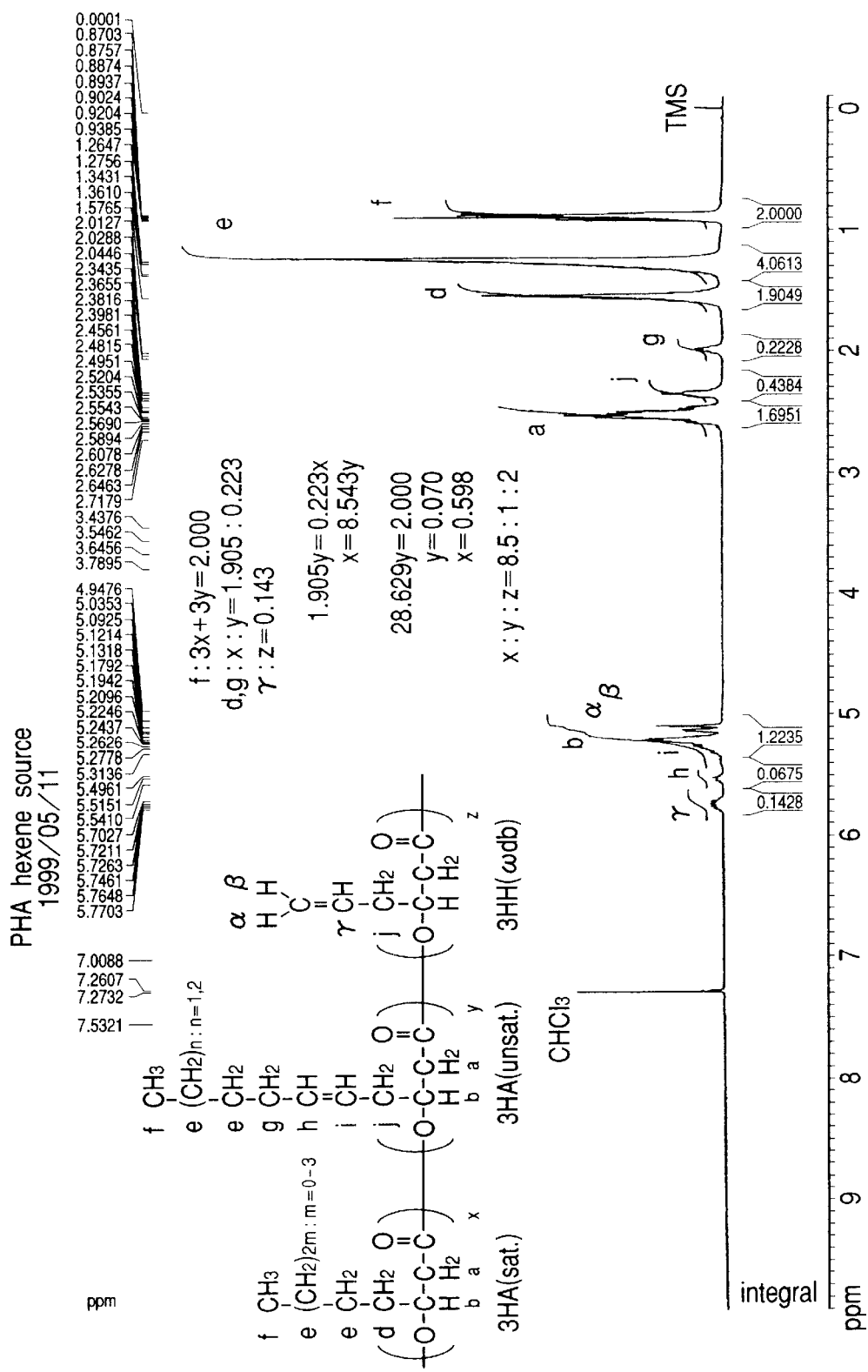
FIG. 1 is an $^1$H-NMR chart of PHA.

The present invention provides a method for producing a PHA containing a monomer unit having a carbon-carbon double bond in the side chain, by growing a microorganism in a medium containing 1-hexene as a sole carbon source.

Preferably, the microorganism is a bacterium of genus Pseudomonas, more preferably, *Pseudomonas cichorii* YN2 (FERM BP-7375).

Taxonomical characteristics of *Pseudomonas cichorii* YN2 are as follows:

Growth temperature: 30° C.

Morphology: rod (0.8×1.5 to 2.0 μm)

Gram staining: gram-negative
Spore formation: negative
Motility: positive
Colony morphology: circular, entire, convex, smooth, glossy, translucent
Catalase: positive
Oxidase: positive
O/F test: non-fermentive
Nitric acid reduction: negative
Indole production: positive
Glucose acidification: negative
Arginine dehydrolase: negative
Urease: negative
Esculin hydrolysis (β-glucosidase): negative
Gelatin hydrolysis (protease): negative
β-galactosidase: negative
Assimilation of compounds:
  glucose: positive
  L-arabinose: positive
  D-mannose: negative
  D-mannitol: negative
  N-acetyl-D-glucosamine: negative
  maltose: negative
  potassium gluconate: positive
  n-capric acid: positive
  adipic acid: negative
  dl-malic acid: positive
  sodium citrate: positive
  phenyl acetate: positive
Production of fluorescent pigment on King's B agar: positive
Growth in 4% NaCl: positive (weak)
Accumulation of poly-β-hydroxybutyrate: negative*
Tween 80 degradation: positive
(* by staining of colonies on the nutrient agar with Sudan Black)

With the above characteristics, the bacterium was determined to be a strain of *Pseudomonas cichorii* according to Bergey's Manual of Determinative Bacteriology, 9th Edition. Further, the PHA production behavior of this strain indicates this being a novel strain, so that it has been deposited in National Institute of Bioscience and Human Technology, Agency of Industrial Science and Technology, 1–3, Higashi 1-chome, Tsukuba-shi, Ibaraki-ken, 305, Japan on Nov. 20, 2000 as FERM BP-7375.

The culture medium used in the present invention may be any mineral salts medium containing phosphate and a nitrogen source such as ammonium salt or nitrate. By controlling the nitrogen concentration can be enhanced the PHA productivity. 1-hexene to be added in the culture medium is volatile, and poorly soluble in water, so that the culture vessel must be tightly closed after securing the required oxygen.

An example of the mineral salt medium composition is shown below.

M9 medium

| | |
|---|---|
| $Na_2HPO_4$ | 6.3 g/l |
| $KH_2PO_4$ | 3.0 g/l |
| NaCl | 0.5 g/l |
| $NH_4Cl$ | 1.0 g/l |
| pH 7.0 | |

1/10 M9 medium

| | |
|---|---|
| $Na_2HPO_4$ | 6.3 g/l |
| $KH_2PO_4$ | 3.0 g/l |
| NaCl | 0.5 g/l |
| $NH_4Cl$ | 0.1 g/l |
| pH 7.0 | |

For better growth and PHA production, the following trace element solution must be added to the above inorganic salt medium to 0.3% (v/v).

Trace Element Solution (g/L)

| | |
|---|---|
| nitrilotriacetic acid | 1.5 |
| $MgSO_4$ | 3.0 |
| $MnSO_4$ | 0.5 |
| NaCl | 1.0 |
| $FeSO_4$ | 0.1 |
| $CaCl_2$ | 0.1 |
| $ZnSO_4$ | 0.1 |
| $CuSO_4$ | 0.1 |
| $AlK(SO_4)_2$ | 0.1 |
| $H_3BO_3$ | 0.1 |
| $Na_2MoO_4$ | 0.1 |
| $NiCl_2$ | 0.1 |

The culture temperature may be any temperature so long as the above strain can grow well, e.g., 15 to 40° C., preferably about 20 to 30° C.

Any culture method can be used in the present invention so long as the above strain can grow and produce PHA, for example, such as liquid culture, solid culture, batch culture, fedbatch culture, semi-continuous culture, and continuous culture.

As for PHA recovery from the cells in the present invention, ordinary chloroform extraction is most convenient. However, where the organic solvent is difficult to use, PHA can be recovered by removing the cell components other than PHA by treating with surfactants such as SDS, enzymes such as lysozyme, agents such as EDTA, sodium hypochlorite and ammonia.

Now the present invention will be described with reference to the following Example, however it is our intention that the scope of the invention be not limited by any of the details of the description.

EXAMPLE

PHA Production by Culturing Strain YN2 with 1-Hexene Carbon Source

Strain YN2 was grown on an M9 agar medium containing 0.1% yeast extract, and a colony was taken and suspended in a sterilized physiological saline to prepare a cell suspension of $OD_{600}$ 1.0.

The suspension was spread on 20 plates of 1/10N-M9 agar not containing a carbon source, and the plates were incubated at 30° C. under 1-hexene atmosphere.

After 4 days incubation, cells were collected, washed with methanol, and the collected cells by centrifugation was dried under a reduced pressure. The dry weight of the cells was 150 mg.

To the dried cells, 50 ml of chloroform was added and stirred at 50° C. for 24 hrs to extract PHA. The chloroform layer was filtrated, concentrated by an evaporator. Cold methanol was added to remove the precipitate, which was then dried under a reduced pressure. Thus, 68 mg of dried PHA was obtained. The PHA weighed to about 45% of the dried cell weight.

The composition of the obtained polymer was determined as follows: 10 mg of the polymer was put into a 25 ml egg-plant type flask and dissolved by adding 2 ml chloroform, to which 2 ml of a methanol solution containing 3% sulfuric acid was added, and reacted at 100° C. under reflux for 3.5 hrs.

After the completion of the reaction, 2 ml water was added to the flask, and the flask was shaken vigorously for 10 min, and left stand for phase separation. The lower chloroform layer was removed and dried over magnesium sulfate. This was then subjected to gas-mass chromatography to identify each methyl hydroxyalkanoate peak by using a gas chromatograph-mass spectrograph (GC-MS; Shimadzu QP-5050, DB-WAX capillary column (J&W). The result is shown in Table 1.

TABLE 1

| Unit | C4 | C6 | C6: | C8 | C8: | C10 | C12 | C12' | C14 | C14: |
|------|-----|------|-----|------|-----|------|------|------|-----|------|
| Area % | 0.5 | 27.2 | 8.0 | 11.9 | 0.5 | 25.7 | 10.3 | 10.9 | 2.5 | 0.6 |

In Table 1, each value represents the peak area (%) in the GC-MS TIC chromatogram.

C4 :3-hydroxybutyric acid

C6 :3-hydroxyhexanoic acid

C6: :3-hydroxyhexenoic acid

C8 :3-hydroxyoctanoic acid

C8: :3-hydroxyoctenoic acid

C10 :3-hydroxydecanoic acid

C11 :3-hydroxyundecanoic acid

C12' :3-HA unit having a double bond or a branch, not identified

C14 :3-hydroxytetradecanoic acid

C14: :presumably 3-hydroxytetradecenoic acid, not identified

The obtained polymer was further analyzed by NMR (FT-NMR:Bruker DPX400, subject nuclides: $^1$H, $^{13}$C, solvent:D-chloroform with TMS).

FIGS. 1 and 2 show the $^1$H-NMR and $^{13}$C-NMR charts. Table 2 shows the peak assignment in $^1$H-NMR.

TABLE 2

| resonant frequency: 400 MHz | |
|---|---|
| δ (ppm) | Assignment |
| 0.88 | m; 2H, f |
| 1.27 | m; 4H, e |
| 1.58 | m; 2H, d |
| 2.03 | m; 0.3H, g |
| 2.37 | m; 0.7H, j |
| 2.60 | m; 1.6H, a |
| 5.09 | s; α |
| 5.13 | d; β |
| 5.18 | m; b |
| 5.28 | m; i |
| 5.52 | m; 0.068H, h |
| 5.73 | m; 0.143H, γ | m:multiplet, d:doublet, s:singlet

As shown above, PHA containing at least 3-hydroxyhexenoic acid units and 3-hydroxyoctenoic acid units is synthesized in *Pseudomonas cichorii* YN2 (FERM BP-7375) by culturing the strain in the presence of 1-hexene.

What is claimed is:

1. A method comprising the steps of:

culturing a bacterium of the genus Pseudomonas being capable of producing a polyhydroxyalkanoate in a culture medium containing 1-hexene as a sole carbon source; and recovering the polyhydroxyalkanoate from the bacterium.

2. The method according to claim 1, wherein the polyhydroxyalkanoate comprises at least one monomer unit of hydroxy-fatty acid having a carbon-carbon double bond.

3. The method according to claim 2, wherein the hydroxy-fatty acid unit is selected from the group consisting of 3-hydroxyhexenoic acid and 3-hydroxyoctenoic acid.

4. The method according to claim 1, wherein the bacterium is *Pseudomonas cichorii* YN2 (FERM BP7375).

5. The method according to claim 2, wherein the bacterium is *Pseudomonas cichorii* YN2 (FERM BP7375).

6. The method according to claim 3, wherein the bacterium is *Pseudomonas cichorii* YN2 (FERM BP7375).

7. A method for producing a polyhydroxyalkanoate comprising the steps of:

culturing a bacterium of the genus Pseudomonas being capable of producing a polyhydroxyalkanoate in a culture medium containing 1-hexene as a carbon source; and recovering the polyhydroxyalkanoate from the bacterium, wherein the polyhydroxyalkanoate comprises a monomer unit derived from 1-hexene.

* * * * *

UNITED STATES PATENT AND TRADEMARK OFFICE
CERTIFICATE OF CORRECTION

PATENT NO.     : 6,492,147 B2
DATED          : December 10, 2002
INVENTOR(S)    : Imamura et al.

It is certified that error appears in the above-identified patent and that said Letters Patent is hereby corrected as shown below:

Title page,
Item [56], References Cited, OTHER PUBLICATIONS, after "Huijberts, et al.", "Unsaturaded" should read -- Unsaturated --.

Column 1,
Line 18, "accumulated" should read -- accumulate --; and
Line 60, "Vol, 12" should read -- Vol. 12 --.

Signed and Sealed this

Fifteenth Day of July, 2003

JAMES E. ROGAN
*Director of the United States Patent and Trademark Office*